US005610519A

United States Patent [19]

Hankui et al.

[11] Patent Number: 5,610,519

[45] Date of Patent: Mar. 11, 1997

[54] DEVICE AND METHOD FOR MEASURING SPECIFIC ABSORPTION RATE OF ELECTROMAGNETIC WAVES IN MODELS OF HUMAN BODIES

[75] Inventors: Eiji Hankui; Takashi Harada, both of Tokyo, Japan

[73] Assignee: NEC Corporation, Japan

[21] Appl. No.: 530,027

[22] Filed: Sep. 19, 1995

[30] Foreign Application Priority Data

Sep. 21, 1994 [JP] Japan .................................. 6-226313

[51] Int. Cl.$^6$ ........................ G01R 33/02; G01R 33/028
[52] U.S. Cl. ............................................. 324/247; 324/244
[58] Field of Search ............................ 324/247, 228, 324/21, 243, 225, 244–263, 95

[56] References Cited

U.S. PATENT DOCUMENTS

| | | | |
|---|---|---|---|
| 3,644,825 | 2/1972 | Davis, Jr. et al. | 324/247 |
| 3,778,703 | 12/1973 | Jackson | 324/247 |
| 4,368,472 | 1/1983 | Gandhi | 343/718 |
| 4,588,993 | 5/1986 | Babij et al. | 343/351 |
| 4,659,984 | 4/1987 | Doss | 324/95 |
| 4,672,309 | 6/1987 | Gandhi | 324/95 |
| 4,913,153 | 4/1990 | Hagmann et al. | 324/127 X |

OTHER PUBLICATIONS

Misra et al, "Response of Electric Field Probes Near a Cylindrical Model of the Human Body", IEEE Transactions on Microwave Theory and Techniques, vol. MTT33, pp. 447–452 (Jun. 1985).

"Guidelines for Protection of Humans in Utilization of Electromagnetic Waves" proposed by Electro–Communication Technology Study Council of Japanese Ministry of Posts and Telecommunications, p. 27 (1990).

N. Kuster et al., "Energy Absorption Mechanism by Biological Bodies in the Near Field of Dipole Antennas Above 300 MHz", IEEE Transactions on Vehicular Technology, vol. 41, No. 1, Feb. 1992, pp. 17–23.

*Primary Examiner*—Sandra L. O'Shea
*Assistant Examiner*—Roger Phillips
*Attorney, Agent, or Firm*—Ostrolenk, Faber, Gerb & Soffen, LLP

[57] ABSTRACT

The device disclosed is for measuring a Specific Absorption Rate (SAR) in a human body exposed to electromagnetic fields radiating from an antenna, and is constituted by a phantom (a model of the human body) and a probe structure. The phantom has equivalent electric constant of permittivity and permeability as those of a human body. The probe structure has a combination of first and second loop probes orthogonal to each other, and is arranged such that the second loop probe receives only a magnetic field that has been reflected from a surface of the phantom. Thus, the magnetic field radiating from the antenna and the magnetic field reflected from a surface of the phantom are distinguished from each other. The reflected magnetic field is corrected and the SAR can be accurately measured.

3 Claims, 5 Drawing Sheets $Hr(X) = Hr \cdot \sin\theta$
$Hr(Y) = Hr \cdot \cos\theta$

DEVICE AND METHOD FOR MEASURING SPECIFIC ABSORPTION RATE OF ELECTROMAGNETIC WAVES IN MODELS OF HUMAN BODIES

BACKGROUND OF THE INVENTION (1) Field of the Invention

The present invention relates to a device and method for measuring a Specific Absorption Rate (SAR) in human bodies exposed to electromagnetic waves from antennas of portable telephones, radio frequency equipment, etc. positioned in the vicinity of human bodies.

(2) Description of the Related Art

One of the basic standard guidelines for protecting human bodies from electromagnetic waves is known as the Specific Absorption Rate (SAR). This represents a value of energy absorption per unit mass when a human body is exposed to electromagnetic waves, and the tolerable value is indicated in, for example, "Guidelines for protection of Humans in Utilization of Electromagnetic Waves" proposed by "Electro-Communication Technology Study Council" of Japanese Ministry of posts and Telecommunications.

Conventionally, there has been a study wherein, by using a phantom (biological body model) having the permittivity and the permeability equivalent to those of biological bodies such as human bodies, the SAR has been measured from the incident magnetic fields on the phantom. This has been proposed by N. Kuster and Q. Balzano under the title "Energy Absorption Mechanism by Biological Bodies in the Near Field of Dipole Antennas Above 300 MHz" in IEEE Transaction on Vehicular Technology, Vol. 41, No. 1, 1992, pp 17–23.

In the conventional SAR measuring system which is adopted in the above proposal and which is illustrated in FIGS. 1A and 1B attached hereto, the electromagnetic waves from half-wave dipole antenna 4 are incident perpendicularly on the phantom 5. The distance between the antenna 4 and the phantom 5 is represented by d. Where the real part of the permittivity of the phantom is represented by $\epsilon$, the conductivity by $\sigma$, the mass density by $\rho$, and the incident magnetic field on the front surface of phantom by Hs, the SAR may be expressed by the following equation:

$$SAR = \frac{\sigma}{\rho} \frac{\omega\mu_o}{\sqrt{\omega^2\epsilon^2 + \sigma^2}} (1 + \alpha\Gamma)^2 |Hs|^2 \quad (1)$$

wherein $\omega$ represents an angular frequency, $\Gamma$ represents a reflection coefficient, $\alpha$ represents a correction coefficient, and $\mu_o = 4\pi \times 10^{-7}$.

The incident magnetic fields are proportional to the antenna currents so that the SAR can be expressed also by the antenna currents. In the half-wave dipole antenna, the SAR maximum value of the phantom is at a portion corresponding to the location of the driving point so that, where the antenna current at the driving point is assumed to be I, the incident magnetic fields may be expressed by the following equation:

$$Hs = I/(2\pi d) \quad (2)$$

The current I is calculated from the magnetic fields 8 radiating from the antenna 4 by using a magnetic field receiving loop probe 7. The probe 7 is placed in such a way that the loop surface becomes perpendicular with respect to the X-axis at a location away by a distance t from the driving point of the probe. At this location, the radiating magnetic fields 8 have only X-direction components.

Normally, the characteristic impedance of the human body is of a lower impedance than $120\pi$ which is the characteristic impedance in air. Thus, the electromagnetic waves radiating from the antenna reflect at the front surface of the phantom. FIG. 3 shows incident waves and reflected waves when the electromagnetic fields are incident on the phantom 5 at an incident angle of $\theta$ and the magnetic fields radiating from the antenna 4. The magnetic fields and the electric fields of the incident waves are represented by Hin and Ein, respectively, the reflected waves are represented by Hr and Er, and the radiating magnetic fields from the antenna are represented by Hi. The X-axis direction component Hr(X) and the Y-axis direction component Hr(Y) of the reflected magnetic fields at the location where the probe is placed may be expressed by the following equations, respectively:

$$Hr(X) = Hr \sin\theta \quad (3)$$

$$Hr(Y) = Hr \cos\theta \quad (4)$$

Therefore, the magnetic fields Hp of the X-axis direction which the probe receives may be expressed by the following equation:

$$Hp = Hi - Hr(X) \quad (5)$$

Where the phantom is located remotely, the reflected magnetic fields attenuate with distance, resulting in a small effect on the phantom. However, where the phantom is located in the vicinity of the antenna, the effect from the reflected waves can no longer be ignored.

When the distance d between the antenna and the phantom is varied, the relation between the reflected magnetic fields Hr(X) in the X-direction and the radiating magnetic fields Hi will be as shown in FIG. 4. When the distance d becomes smaller than 3 cm, the reflected magnetic fields increase to more than 25%. Thus, the problem in the probe arrangement as above is that the probe receiving the magnetic fields for the calculation of the antenna currents results in being measured smaller than the actual value, which leads to a large SAR error.

SUMMARY OF THE INVENTION

An object of the present invention, therefore, is to overcome the problems existing in the prior art and to provide a device and a method for measuring the SAR, wherein the reflected magnetic fields are corrected and the SAR is accurately measured.

According to a first aspect of the invention, there is provided a device for measuring a Specific Absorption Rate (SAR) in a human body exposed to electromagnetic fields radiating from an antenna, the device comprising:

a phantom having equivalent electric constant of permittivity and permeability as those of a human body; and a probe structure having a combination of first and second loop probes orthogonal to each other, the probe structure being arranged such that the second loop probe receives only a magnetic field that has been reflected from a surface of the phantom.

According to a second aspect of the invention, there is provided a method for measuring a Specific Absorption Rate (SAR) in phantom exposed to electromagnetic fields radiating from an antenna, by using a probe structure having a combination of first and Second loop probes orthogonal to each other, the method comprising the steps of:

disposing the first and second loop probes such that the second loop probe receives only a magnetic field that has been reflected from a surface of the phantom; and distinguishing a magnetic field radiating from the antenna and the magnetic field that has been reflected from the surface of the phantom thereby correcting the magnetic field that has been reflected.

Further, according to the invention, by using the probe structure constituted by two loop probes which are orthogonal to each other, the radiating magnetic field from the antenna and the reflected magnetic field from a surface of the phantom are distinguished from each other, whereby the reflected magnetic field is corrected.

The reflected magnetic field is corrected in the manner explained hereinafter.

In FIG. 3, the reflected magnetic field Hr(X) may be expressed, using the incident angle θ and the Y-direction component Hr(Y), by the equations (3) and (4).

$$Hr(X)=Hr\cdot\sin\theta=Hr(Y)\cdot\tan\theta=Hr(Y)\cdot t/2d \qquad (6)$$

Therefore, the radiating magnetic field Hi from the antenna may be expressed by:

$$Hi=Hp+Hr(X)=Hp+Hr(Y)\cdot t/2d \qquad (7)$$

By measuring the Y-direction component of the reflected magnetic field at the location where the probe is placed, it is possible to correct the influence of the reflected magnetic field.

BRIEF DESCRIPTION OF THE DRAWINGS

The above and other objects, features and advantages of the present invention will be apparent from the following description of preferred embodiments of the invention explained with reference to the accompanying drawings, in which.

PREFERRED EMBODIMENT OF THE INVENTION

Now, a preferred embodiment of the invention is explained with reference to the drawings.

Figure 1A:
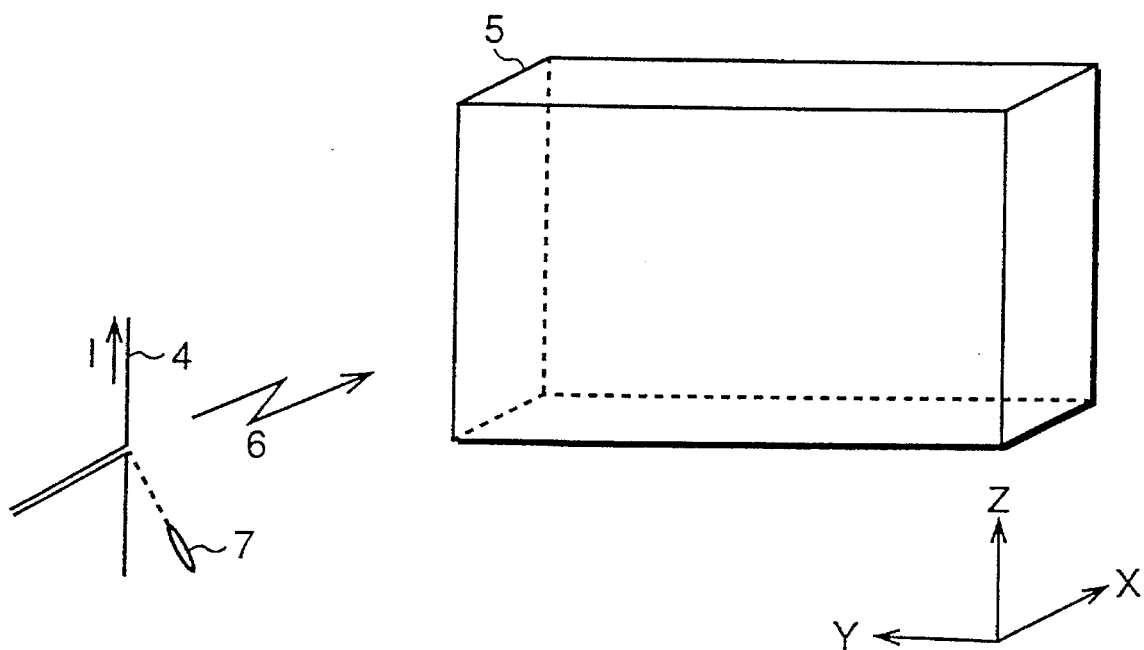
FIGS. 1A and 1B are diagrams showing an arrangement of a conventional SAR measuring device, FIG. 1A being a perspective view thereof and FIG. 1B being a top view thereof.
Figure 1B:
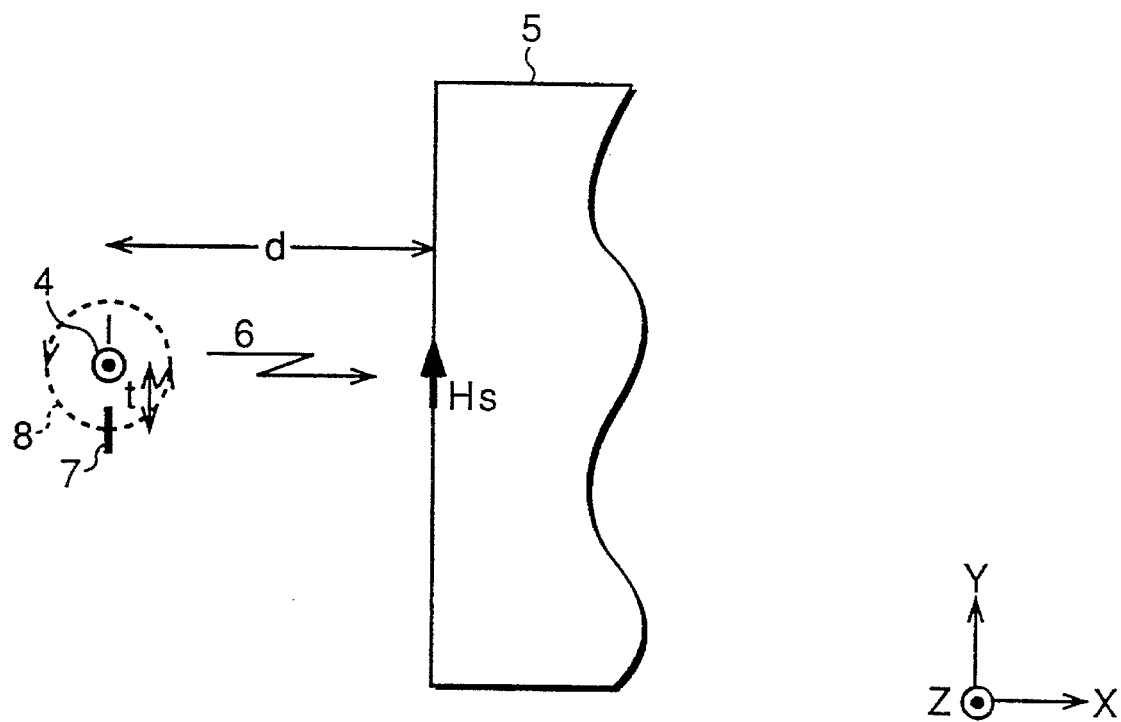
Figure 2A:
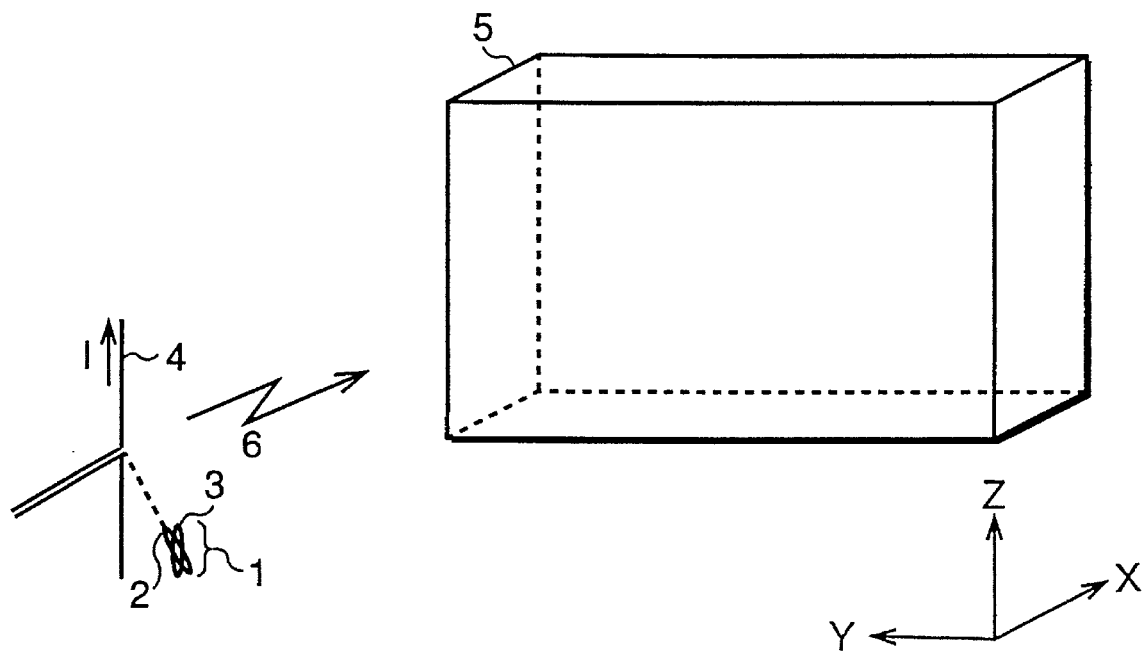
FIGS. 2A and 2B are diagrams showing an arrangement of an SAR measuring device according to the present invention, FIG. 2A being a perspective view thereof and FIG. 2B being a top view thereof.
Figure 2B:
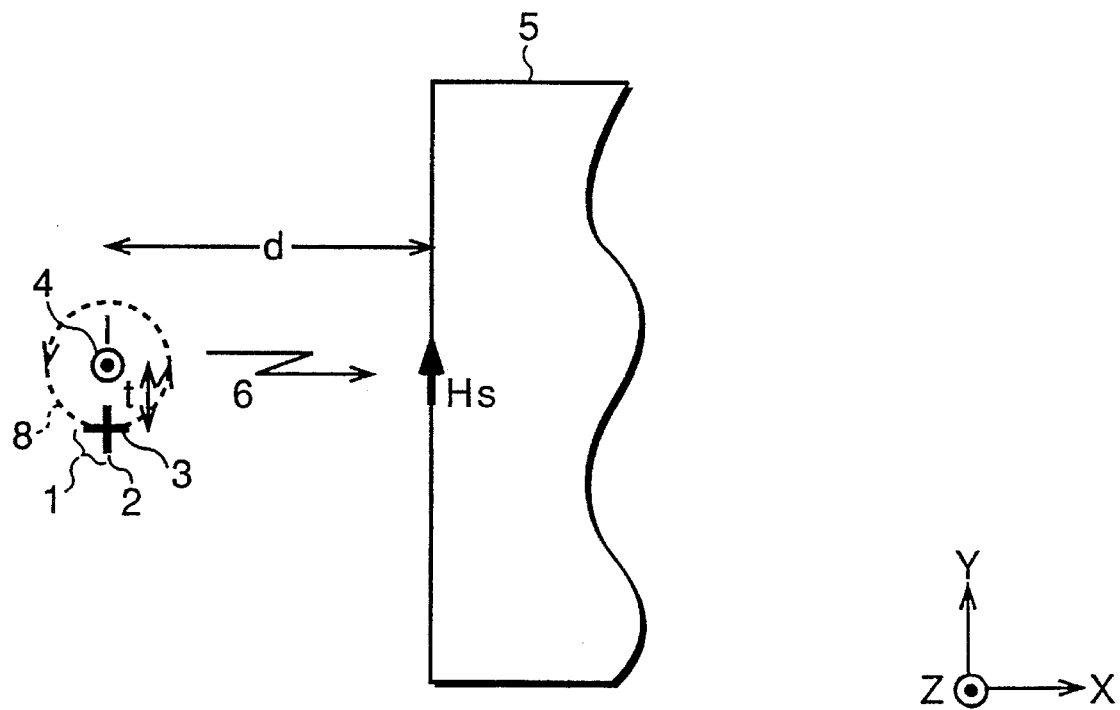
Figure 3:
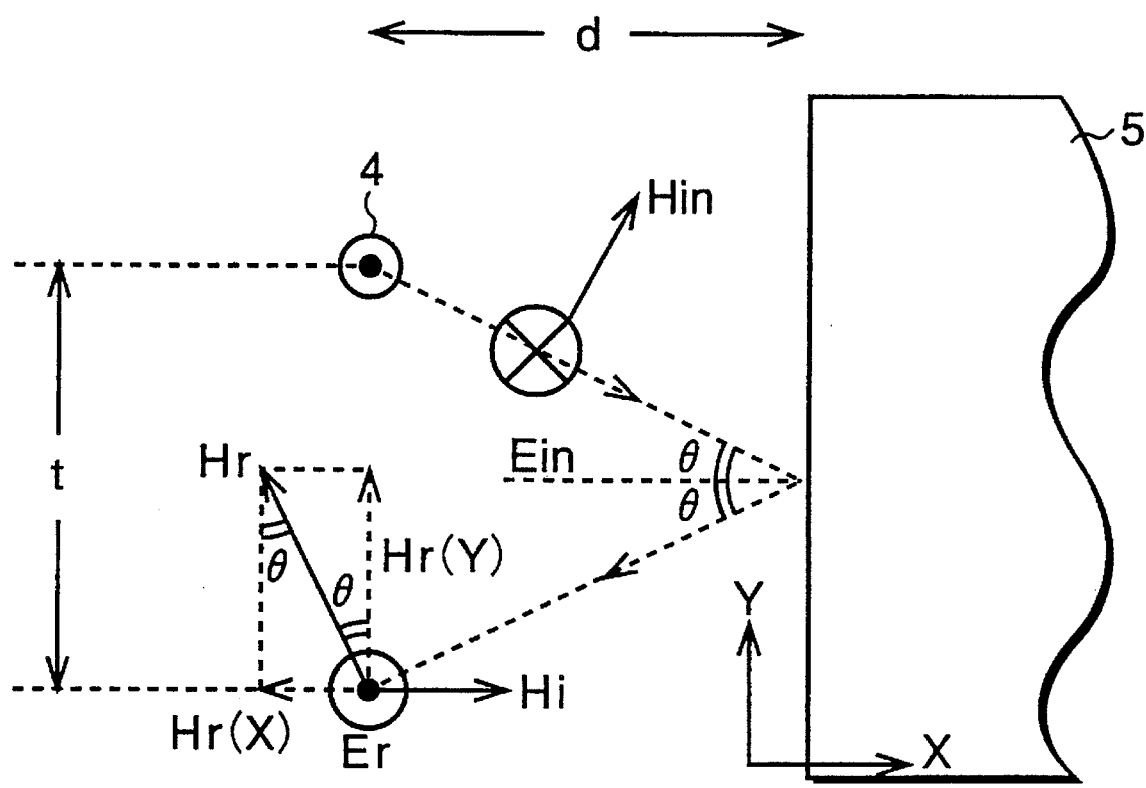
FIG. 3 is a diagram for use in explaining the incident waves and the reflected waves when the magnetic fields are incident on the phantom at an incident angle of θ, and the magnetic fields radiating from the antenna.
Figure 4:
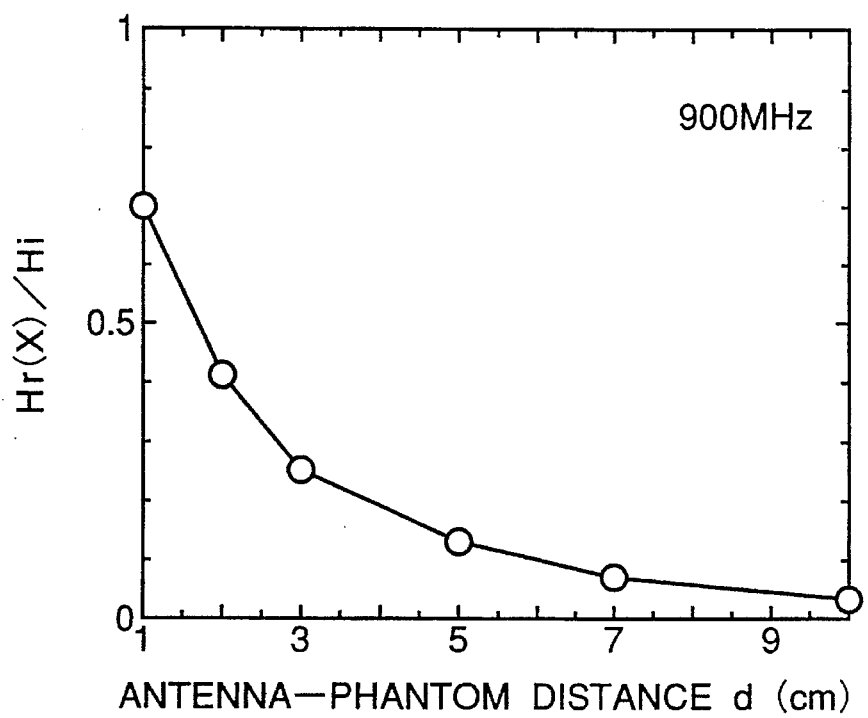
FIG. 4 is a diagram showing the relationship between the reflected magnetic field in the X-direction and the radiating magnetic field when the distance d between the antenna and the phantom is varied.

FIGS. 2A and 2B diagrammatically show an SAR measuring device of an embodiment according to the invention.

In carrying out the measuring operation, waves of 900 MHz from the antenna 4 irradiate the phantom 5. The output power of the antenna 4 is on the order of 1 W. The phantom 5 has the real part of a relative permittivity of 41.1, a conductivity of 0.88 S/m, and a mass density of 2.4 g/cm$^3$. The orthogonal probe structure 1 is constituted by two loop probes 2 and 3 having a common center and having loop surfaces orthogonal to each other. The probe structure 1 is placed at a location away by a distance t from the antenna 4. At this location, by placing the first probe 2 perpendicular to the X-axis, it is possible to measure only the radiating magnetic field 8 and, by placing the second probe 3 perpendicular to the Y-axis, it is possible to measure only the reflected magnetic field. After the reflected magnetic field is corrected, the antenna currents are calculated.

Figure 5:
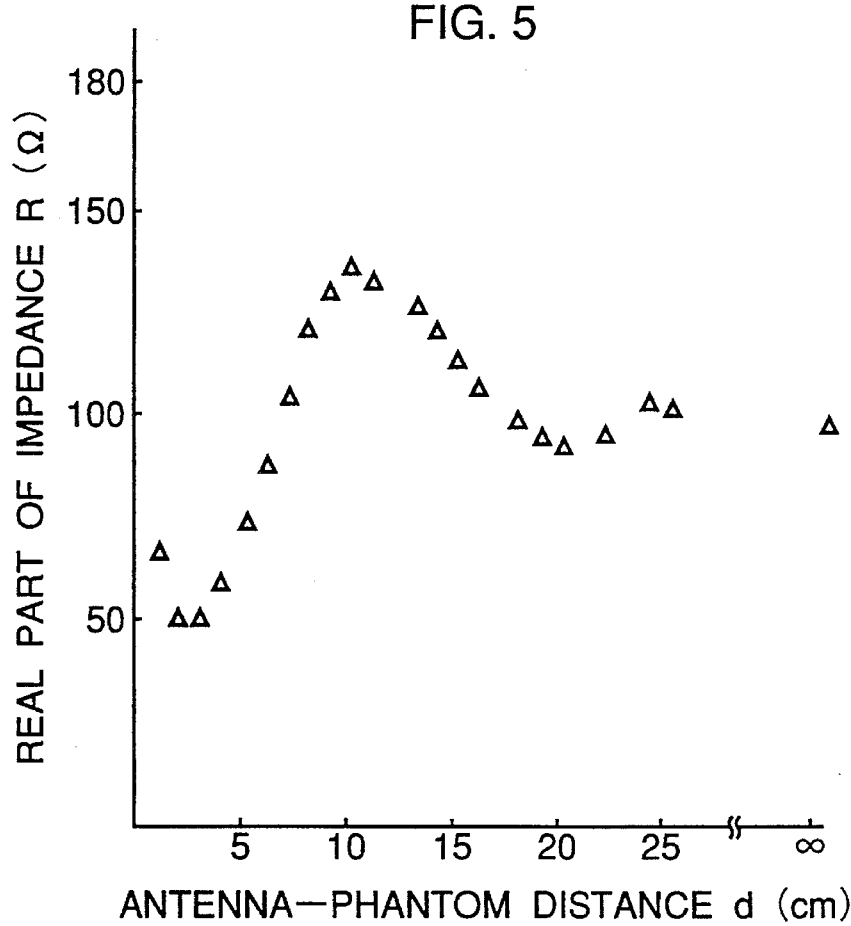
FIG. 5 is a diagram showing the real part of the impedance at the driving point when the distance d between the antenna and the phantom is varied.

FIG. 5 shows the real part of the impedance R (Ω) at the driving point of the antenna when the distance d is varied. As the probe gets closer to the phantom, the value of R changes and becomes a minimum at d=2 cm and reaches a maximum at d=10 cm where the distance is about ¼ and, with the repetition of oscillations, R becomes a minimum again at d=20 cm.

Figure 6:
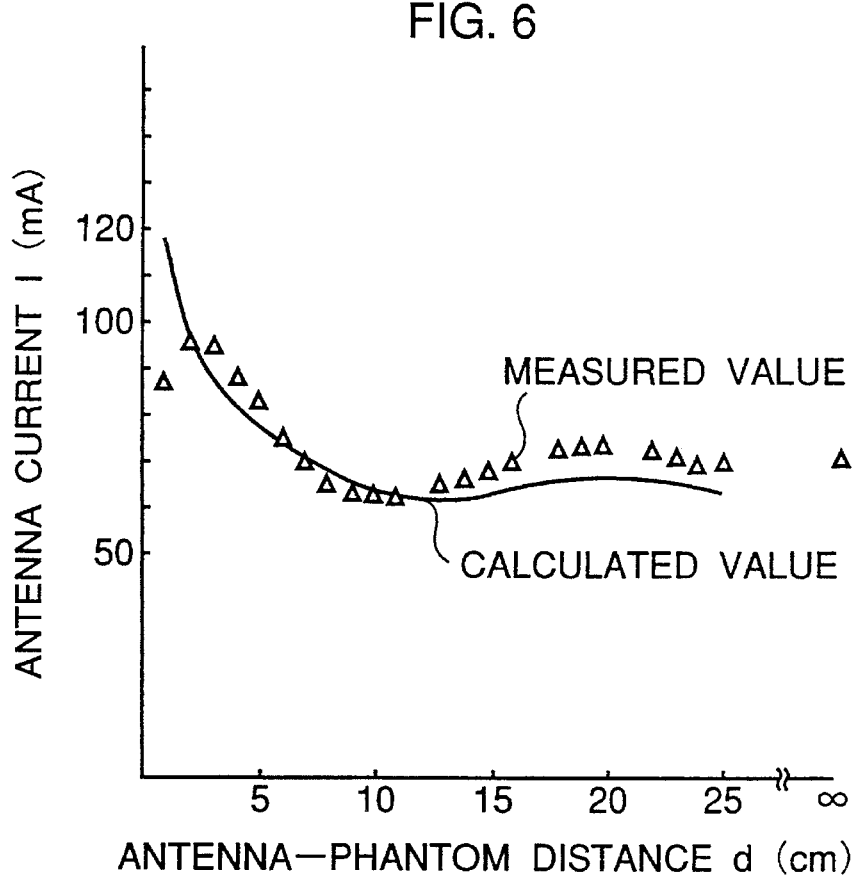
FIG. 6 is a diagram showing antenna currents at the driving point when the distance d between the antenna and the phantom is varied.

FIG. 6 shows the relationship between the antenna currents I at the driving point and the distance d when a probe having a diameter of 10 mm is used. Symbol Δ represents the measured value, the solid line represents the calculated value derived from the impedance at the driving point. The probe is placed 35 mm away from the driving point. The antenna currents become a minimum at d=10 cm and maximum at d=20 cm, with a trend wherein an increase and a decrease thereof are qualitatively opposite with respect to R. Since the measured values substantially coincide with the calculated values, it can be appreciated that the antenna currents are calculated after the reflected magnetic fields have been corrected.

Figure 7:
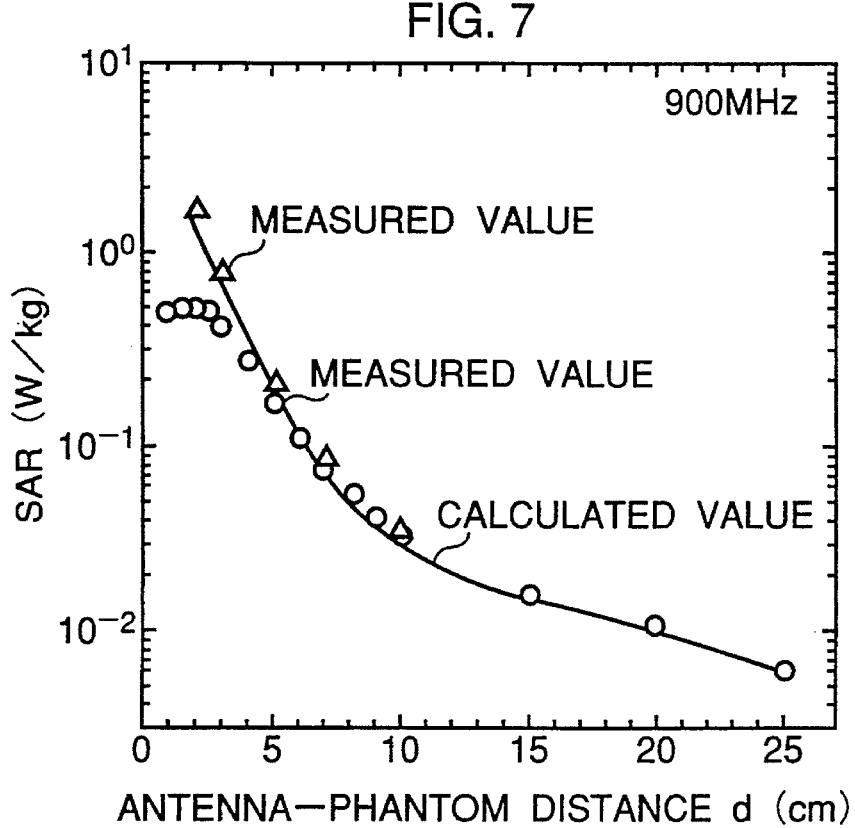
FIG. 7 is a diagram showing the SAR when the distance d between the antenna and the phantom is varied.

FIG. 7 shows the relationship between the SAR (W/kg) of the phantom and the distance d. In the graph, the symbol Δ represents the reflected waves having been corrected, ○ represents the reflected waves not having been corrected, and the solid line represents the calculated values of the antenna currents. Whereas, when the distance d becomes larger, the measured values (Δ and ○) become coincident with each other, when the distance d becomes smaller than 3 cm, the value without having been corrected becomes smaller and results in different characteristics. The measured values after the reflected waves have been corrected do coincide with the calculated values very well. From this, the effectiveness of a method in which the reflected waves are corrected can be appreciated.

According to the invention, the phantom is used for making the evaluation. Of course, it is possible to evaluate biological bodies such as human and animal bodies similarly in place of the phantom.

While the invention has been described in its preferred embodiments, it is to be understood that the words which have been used are words of description rather than limitation and that changes within the purview of the appended claims may be made without departing from the scope of the invention as defined by the claims.

What is claimed is:

1. A device for measuring a Specific Absorption Rate (SAR) in a human body exposed to electromagnetic fields radiating from an antenna, the device comprising:

a phantom having a surface and an equivalent electric constant of permittivity and permeability as those of a human body; and a probe structure having a combination of first loop probe and second loop probe orthogonal to each other, said first loop probe being disposed in parallel to the surface of said phantom and said second loop probe being disposed perpendicular to the surface of said phantom, said probe structure being arranged such that said second loop probe receives only a magnetic field that has been reflected from the surface of said phantom.

2. The device for measuring a Specific Absorption Rate according to claim 1, in which said first loop probe is disposed perpendicular to said electromagnetic fields and the second loop probe is disposed perpendicular to said first loop probe such that said second loop probe measures a component of the reflected magnetic field only in a direction of said first loop probe.

3. A method for measuring a Specific Absorption Rate (SAR) in a phantom having a surface and being exposed to electromagnetic fields radiating from an antenna, by using a probe structure having a combination of first and second loop probes orthogonal to each other, said method comprising the steps of:

disposing said first and second loop probes such that said second loop probe receives only a magnetic field that has been reflected from the surface of said phantom; and distinguishing a magnetic field radiating from said antenna and the magnetic field that has been reflected from the surface of said phantom thereby correcting said magnetic field that has been reflected.

* * * * *